United States Patent
Weingarten et al.

(10) Patent No.: US 11,213,358 B2
(45) Date of Patent: *Jan. 4, 2022

(54) MULTI-RIGID REGISTRATION OF MAGNETIC NAVIGATION TO A COMPUTED TOMOGRAPHY VOLUME

(71) Applicant: Covidien LP, Mansfield, MA (US)

(72) Inventors: Oren P. Weingarten, Hod-Hasharon (IL); Alexander Nepomniashchy, Herzlia (IL)

(73) Assignee: Covidien LP, Mansfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/868,731

(22) Filed: May 7, 2020

(65) Prior Publication Data

US 2020/0261165 A1   Aug. 20, 2020

Related U.S. Application Data

(63) Continuation of application No. 16/196,032, filed on Nov. 20, 2018, now Pat. No. 10,646,284.

(Continued)

(51) Int. Cl.
*G06K 9/00*   (2006.01)
*A61B 34/20*  (2016.01)
(Continued)

(52) U.S. Cl.
CPC ............... *A61B 34/20* (2016.02); *A61B 34/10* (2016.02); *A61B 90/37* (2016.02); *G16H 50/50* (2018.01);
(Continued)

(58) Field of Classification Search
CPC ......... A61B 34/10; A61B 34/20; A61B 90/37; A61B 2034/107; A61B 2034/2051;
(Continued)

(56) References Cited

U.S. PATENT DOCUMENTS 5,727,554 A   3/1998   Kalend et al.
6,076,005 A   6/2000   Sontag et al.
(Continued)

FOREIGN PATENT DOCUMENTS

JP   2006512950 A   4/2006
WO  2011101754 A1   8/2011
(Continued)

OTHER PUBLICATIONS

International Search Report and Written Opinion for application No. PCT/US2018/062199 dated Mar. 19, 2019.

*Primary Examiner* — Atiba O Fitzpatrick
(74) *Attorney, Agent, or Firm* — Carter, DeLuca & Farrell LLP

(57) ABSTRACT

Devices, systems, methods, and computer-readable media for registering an electromagnetic registration of a luminal network to a 3D model of the luminal network include accessing a 3D model of a luminal network based on computed tomographic (CT) images of the luminal network, selecting a plurality of reference points within the 3D model of the luminal network, obtaining a plurality of survey points within the luminal network, dividing the 3D model of the luminal network and the luminal network into a plurality of regions, assigning a plurality of weights to the plurality of regions, determining an alignment of the plurality of reference points with the plurality of survey points based on the plurality of weights, and generating a registration based on the alignment, the registration enabling conversion of the plurality of survey points within the luminal network to points within the 3D model of the luminal network.

20 Claims, 6 Drawing Sheets

Related U.S. Application Data

(60) Provisional application No. 62/594,623, filed on Dec. 5, 2017.

(51) Int. Cl.
   *A61B 34/10* (2016.01)
   *A61B 90/00* (2016.01)
   *G16H 50/50* (2018.01)
   *A61B 6/00* (2006.01)
   *A61B 6/03* (2006.01)
   *A61B 17/00* (2006.01)

(52) U.S. Cl.
   CPC .............. *A61B 6/032* (2013.01); *A61B 6/5235* (2013.01); *A61B 2017/00809* (2013.01); *A61B 2034/105* (2016.02); *A61B 2034/107* (2016.02); *A61B 2034/2051* (2016.02); *A61B 2034/2068* (2016.02); *A61B 2034/2072* (2016.02); *A61B 2090/367* (2016.02); *A61B 2090/3762* (2016.02); *A61B 2090/3925* (2016.02)

(58) Field of Classification Search
   CPC ...... A61B 2034/2068; A61B 2090/367; A61B 2090/3762; A61B 6/032; A61B 6/5235; G16H 50/50
   See application file for complete search history.

(56) References Cited

U.S. PATENT DOCUMENTS

| | | | |
|---|---|---|---|
| 6,144,875 A | 11/2000 | Schweikard et al. | |
| 6,188,355 B1 | 2/2001 | Gilboa | |
| 6,473,635 B1 | 10/2002 | Rasche | |
| 6,501,981 B1 | 12/2002 | Schweikard et al. | |
| 6,580,938 B1 | 6/2003 | Acker | |
| 6,865,253 B2 | 3/2005 | Blumhofer et al. | |
| 7,123,758 B2 | 10/2006 | Jeung et al. | |
| 7,213,820 B2 | 5/2007 | Drummond | |
| 7,233,280 B2 | 6/2007 | Mor et al. | |
| 7,318,805 B2 | 1/2008 | Schweikard et al. | |
| 7,403,638 B2 | 7/2008 | Jeung et al. | |
| 7,853,308 B2 | 12/2010 | Sauer et al. | |
| 8,195,269 B2 * | 6/2012 | Bogoni | A61B 6/5217 600/407 |
| 8,200,315 B2 | 6/2012 | Mostafavi | |
| 8,233,688 B2 | 7/2012 | Soubelet et al. | |
| 8,295,435 B2 | 10/2012 | Wang et al. | |
| 8,331,532 B2 | 12/2012 | Nord et al. | |
| 8,744,045 B2 | 6/2014 | Nord et al. | |
| 10,646,284 B2 | 5/2020 | Weingarten et al. | |
| 2006/0106283 A1 | 5/2006 | Wallace et al. | |
| 2008/0240536 A1 | 10/2008 | Soubelet et al. | |
| 2011/0085720 A1 | 4/2011 | Averbuch | |
| 2011/0184238 A1 | 7/2011 | Higgins et al. | |
| 2012/0172712 A1 | 7/2012 | Bar-Tal | |
| 2012/0203065 A1 * | 8/2012 | Higgins | A61B 6/5247 600/109 |
| 2012/0288173 A1 | 11/2012 | Rai et al. | |
| 2014/0270441 A1 | 9/2014 | Baker | |
| 2014/0281961 A1 | 9/2014 | Baker | |
| 2014/0282216 A1 | 9/2014 | Baker | |
| 2015/0305650 A1 | 10/2015 | Hunter et al. | |
| 2016/0000356 A1 * | 1/2016 | Brown | A61B 5/066 600/424 |
| 2018/0235709 A1 | 8/2018 | Donhowe | |

FOREIGN PATENT DOCUMENTS

| | | |
|---|---|---|
| WO | 2015173668 A1 | 11/2015 |
| WO | 2017049163 A1 | 3/2017 |

* cited by examiner

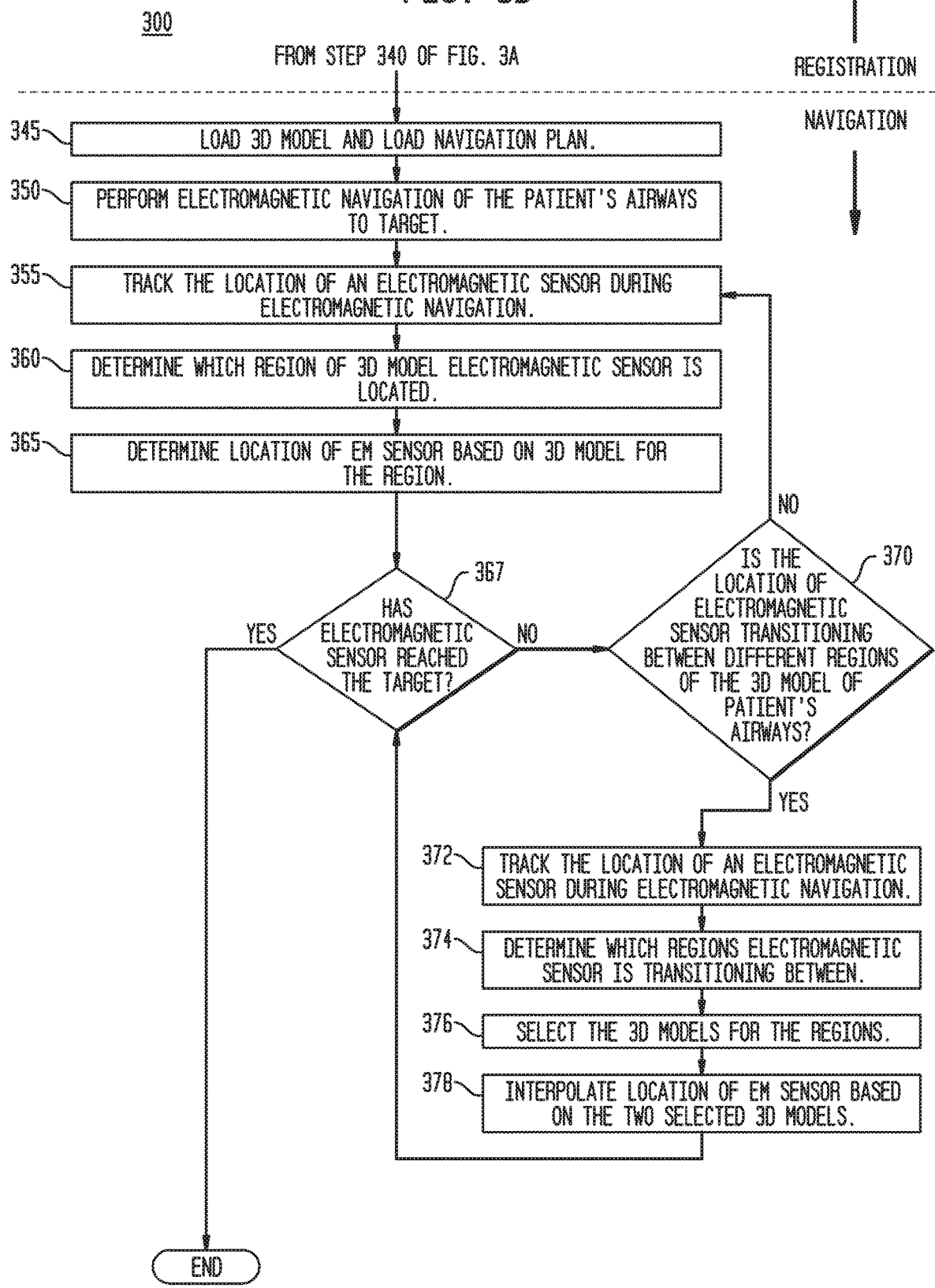

MULTI-RIGID REGISTRATION OF MAGNETIC NAVIGATION TO A COMPUTED TOMOGRAPHY VOLUME

CROSS REFERENCE TO RELATED APPLICATIONS

This application is a continuation of U.S. patent application Ser. No. 16/196,032, filed on Nov. 20, 2018, now U.S. Pat. No. 10,646,284, which claims the benefit of the filing date of provisional U.S. Patent Application No. 62/594,623, filed on Dec. 5, 2017.

FIELD

The present disclosure relates to bronchial registration and, more particularly to devices, systems, methods, and computer-readable media automatically registering a three-dimensional (3D) electromagnetic navigation generated model of a patient's airways with a 3D computed tomographic (CT) scan generated model of the patient's airways for each region of the patient's airways based on a weighting metric.

BACKGROUND

A common device for inspecting the airway of a patient is a bronchoscope. Typically, the bronchoscope is inserted into a patient's airways through the patient's nose or mouth and can extend into the lungs of the patient. A typical bronchoscope includes an elongated flexible tube having an illumination assembly for illuminating the region distal to the bronchoscope's tip, an imaging assembly for providing a video image from the bronchoscope's tip, and a working channel through which instruments, e.g., diagnostic instruments such as biopsy tools, therapeutic instruments can be inserted.

Bronchoscopes, however, are limited in how far they may be advanced through the airways due to their size. Where the bronchoscope is too large to reach a target location deep in the lungs, a clinician may utilize certain real-time imaging modalities such as computed tomography or fluoroscopy. CT or fluoroscopic images, while useful, present certain drawbacks for navigation as it is often difficult to distinguish luminal passageways from solid tissue. Moreover, the images generated are two-dimensional whereas navigating the airways of a patient requires the ability to maneuver in three dimensions.

To address these issues, systems have been developed that enable the development of three-dimensional models of the airways or other luminal networks, typically from a series of computed tomography (CT) images. One such system has been developed as part of the ILOGIC® ELECTROMAGNETIC NAVIGATION BRONCHOSCOPY® (ENB™) system currently sold by Medtronic PLC. The details of such a system are described in commonly assigned U.S. Pat. No. 7,213,820, entitled ENDOSCOPE STRUCTURES AND TECHNIQUES FOR NAVIGATING TO A TARGET IN BRANCHED STRUCTURE, filed on Mar. 29, 2004, by Gilboa, the entire contents of which are incorporated herein by reference.

During the ENB procedures it is important to register the magnetic navigation space to the patient's CT scan. As understood in the art, "registration" refers to a translation, mapping, transformation, or the like, which converts locations or coordinates in one space to locations or coordinates in another space. In order to perform such registration, several methods have been developed. One method, known as manual registration, is based on the visual identification with the bronchoscope of the main airways branching points and associating them with the points visually identified on the CT scans. During the ENB procedure the user navigates the bronchoscope with catheter fitted with the magnetic sensing coil to the branching points in the airways and manually generates the associations between the branching points and the locations in the magnetic navigation space. Another method, known as automatic registration, is based on collection of the point cloud from the airways (called survey) using a catheter with the magnetic sensor at its tip, and then fitting the survey to the image of the airway tree derived from the CT scan using a segmentation algorithm and is further described in commonly owned U.S. Patent Publication No. 2011/0085720, entitled "AUTOMATIC REGISTRATION TECHNIQUE," filed on May 14, 2010, by Averbuch et al., the entire contents of all of which are incorporated herein by reference.

While the system as described in U.S. Pat. No. 7,213,820 and U.S. Publication No. 2011/0085720 are quite capable, there is always a need for development of improvements and additions to such systems.

SUMMARY

Provided in accordance with the present disclosure are devices, systems, and methods for generating multiple registrations of an electromagnetic navigation with a patient's CT scan volumetric model and dynamically determining which of the multiple registrations is to be used.

In an aspect of the present disclosure, the present disclosure includes a method of registering an electromagnetic navigation of a luminal network to a 3D model of the luminal network. The method includes accessing a 3D model of a luminal network, where the 3D model is based on computed tomographic (CT) images of the luminal network, selecting reference points within the 3D model of the luminal network, obtaining survey points within the luminal network, dividing the 3D model of the luminal network and the luminal network into regions, assigning weights to the regions, determining an alignment of the reference points with the survey points based on the weights, and generating a registration based on the alignment, where the registration enables conversion of locations within the luminal network to locations within the 3D model of the luminal network.

In various embodiments, the luminal network is an airway of a patient. In various embodiments, the 3D model is a model of the airway of the patient.

In various embodiments, the method further includes determining which region each of the plurality of survey points is obtained from, and assigning a corresponding weight to each survey point based on which region each of the survey points is obtained.

In various embodiments, determining an alignment of the reference points with the survey points includes minimizing a divergence between the reference points and the survey points based on the corresponding weight assigned to each of the survey points.

In various embodiments, the method includes, for each particular region of the regions: assigning particular weights to the regions, where the particular weights favor the particular region, minimizing a divergence between the reference points and the survey points based on the particular weights, where the minimized divergence corresponds to a particular alignment, and generating a particular registration based on the particular alignment, where the particular registration is associated with the particular region and enables conversion of locations within the luminal network to locations within the 3D model of the luminal network.

In various embodiments, the regions include transition regions. In various embodiments, the regions include a right lung region, a central region, and a left lung region, and the transition regions include left-central region and right-central region.

In accordance with another aspect, the present disclosure includes a system for updating a 3D model of a luminal network. The system includes a location sensor capable of being navigated within a luminal network inside a patient's body, an electromagnetic field generator configured to detect a location of the location sensor as it is navigated within the luminal network, and a computing device that includes a processor and a memory storing instructions. When the instructions are executed by the processor, they cause the computing device to access a 3D model of the luminal network based on computed tomographic (CT) images of the luminal network, select reference points within the 3D model of the luminal network, obtain survey points within the luminal network, where the survey points are generated by the location sensor and the electromagnetic field generator, divide the 3D model of the luminal network and the luminal network into regions, assign weights to the regions, determine an alignment of the reference points with the survey points based on the weights, and generate a registration based on the alignment, where the registration enables conversion of the survey points within the luminal network to points within the 3D model of the luminal network.

In various embodiments, the instructions, when executed by the processor, further cause the computing device to determine which region of the regions each of the survey points is obtained, based on detected locations of the location sensor, and assign a corresponding weight to each of the survey points based on which region each of the survey points is obtained. The instructions, when executed by the processor, further cause the computing device to minimize a divergence between the reference points and the survey points based on the corresponding weight assigned to each of the plurality of survey points.

In various embodiments, the instructions, when executed by the processor, further cause the computing device to, for each particular region of the plurality of regions: assign particular weights to the regions, where the particular weights favor the particular region, minimize a divergence between the reference points and the survey points based on the particular weights, where the minimized divergence corresponds to a particular alignment, and generate a particular registration based on the particular alignment, where the particular registration is associated with the particular region and enables conversion of locations within the luminal network to locations within the 3D model of the luminal network.

In various embodiments, the regions include transition regions. In various embodiments, the regions include a right lung region, a central region, and a left lung region, and the transition regions include a left-central region and a right-central region.

In various embodiments, the instructions, when executed by the processor, further cause the computing device to determine that a location of the location sensor is within a transition region, determine which regions of the regions the location sensor is transitioning between, and interpolate a location within the 3D model of the luminal network based on registrations associated with the regions the location sensor is transitioning between.

Any of the above aspects and embodiments of the present disclosure may be combined without departing from the scope of the present disclosure.

BRIEF DESCRIPTION OF THE DRAWINGS

Objects and features of the presently disclosed system and method will become apparent to those of ordinary skill in the art when descriptions of various embodiments thereof are read with reference to the accompanying drawings, wherein:

FIGS. 3A and 3B is a flowchart of a method of registering electromagnetic navigation within a luminal network to a 3D model of the luminal network, provided in accordance with an embodiment of the present disclosure.

DETAILED DESCRIPTION

The present disclosure is directed to devices, systems, methods, and computer-readable media for registering a 3D bronchial tree model (hereinafter referred to as a "3D model") with a patient's airways based on electromagnetic navigation. "Registration" refers to a translation, mapping, transformation, or the like, which converts locations or coordinates in one space to locations or coordinates in another space. The registration disclosed in commonly owned U.S. Patent Publication No. 2011/0085720 titled "Automatic Registration" is referred to as rigid. The technology of the present disclosure is herein referred to as "multi-rigid" registration and as "optimized region registration." The present disclosure provides increased registration accuracy by accounting for the flexibility of the lungs and focusing on one region of the lungs at a time, as further described herein. Using the technology of the present disclosure, multiple registrations can be generated, each corresponding to different region of the lungs and airways.

Due to the flexibility of the lungs, the actual shape of the lungs during the time of a surgical procedure can be deformed or different from the shape at the time of the CT scan and/or initial registration, resulting in the reduction of the navigation accuracy. This deformation due to the flexibility of the lungs may be due to several differences, such as: (1) the CT scan being performed while the patient is holding her breath after a full inhale, whereas during the surgical procedure, both registration and navigation, the patient is sedated and breathing normally; (2) the patient may be horizontal for a much longer period during the surgical procedure thereby causing increased deformation; (3) during the surgical procedure, while the bronchoscope is inside of the patient, the head, neck, and superior part of the chest may also become deformed; and/or (4) often the CT scan is performed on a concave bed while the surgical procedure is generally performed while the patient is lying flat. Thus, the present disclosure includes devices, systems, methods, and computer-readable media to perform the registration of magnetic navigation to the CT scans volumetric models (known as antenna-to-CT registration), particularly as it relates at or around a navigation target using a weighting metric to improve accuracy of 3D model of the airways to account for increased deformation of the airways during a bronchoscopic procedure. In addition, the present disclosure relates to registering multiple rigid registrations based on the electromagnetic navigation and dynamically determining which of the rigid multiple registrations is to be used during navigation.

Figure 1:
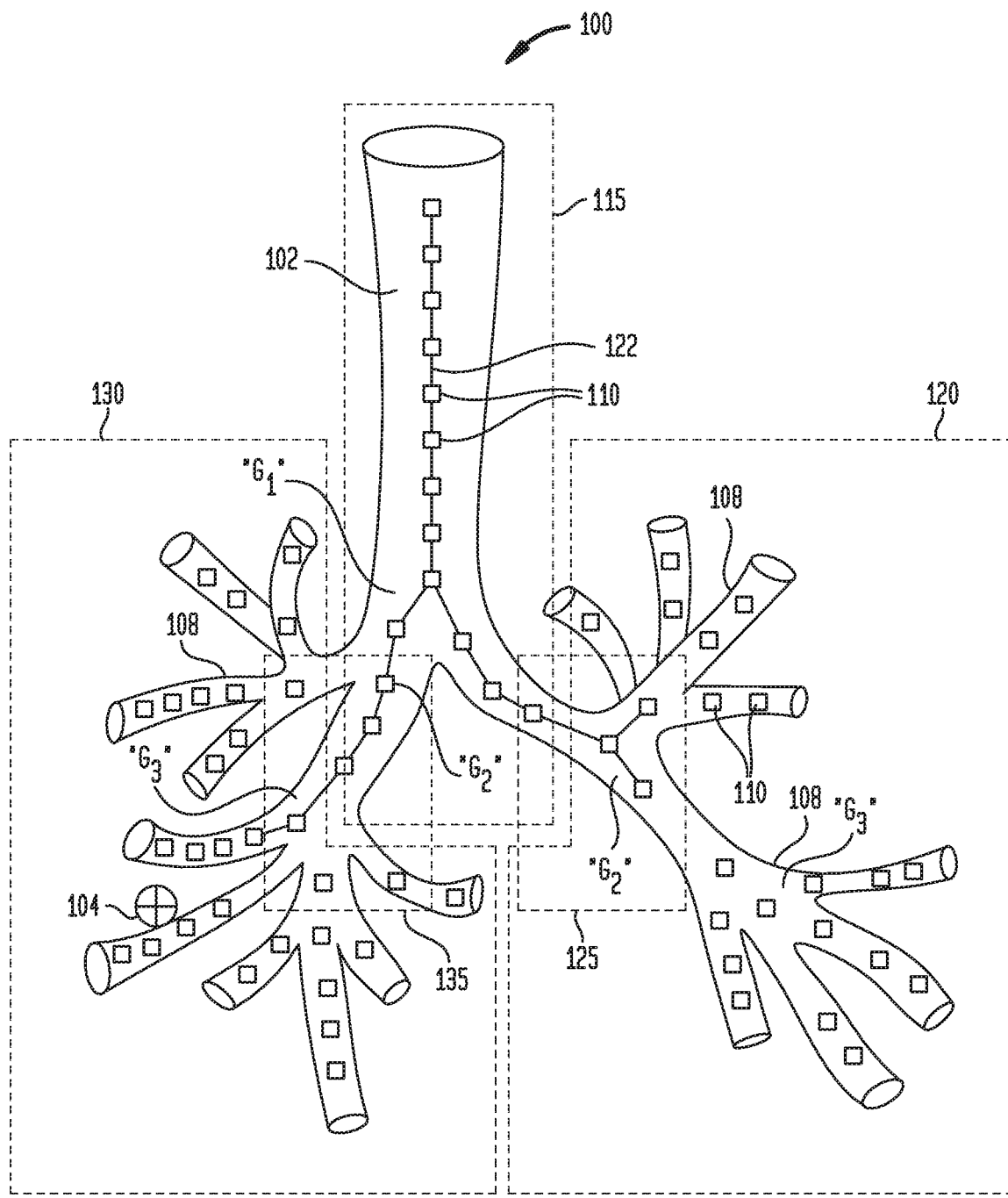
FIG. 1 is a view of 3D volumetric model of the luminal network and divided into regions, provided in accordance with an embodiment of the present disclosure.

FIG. 1 is an illustration of 3D model 100 of a patient's airways generated based on a computer tomographic (CT) scan. As shown in FIG. 1, 3D model 100 includes an airway tree 102, target 104, and airway branches 108 originating from generation bifurcations "$G_1$"-"$G_3$" in airway tree 102. 3D model 100 is divided into a plurality of regions. Generation bifurcations "$G_1$"-"$G_3$" are locations within 3D model 100 where one airway branch 108 breaks into two or more smaller airways. Although, 3D model 100 only illustrates airway branches 108 up to the third generation bifurcation, it is understood that in practice, 3D model 100 may have up to 23 generation bifurcations.

As illustrated in FIG. 1, central region 115 includes the trachea and surrounding airways, left lung region 120 includes the airways of the left lung, and right lung region 130 includes the airways of right lung. Additionally, 3D model 100 includes two transition regions: right-central region 135 and left-central region 125. It is further contemplated that, although these five specific regions are listed, where necessary, additional regions and transition regions may be included in order to increase the number of multiple registrations and thus the accuracy of 3D model 100.

Figure 2A:
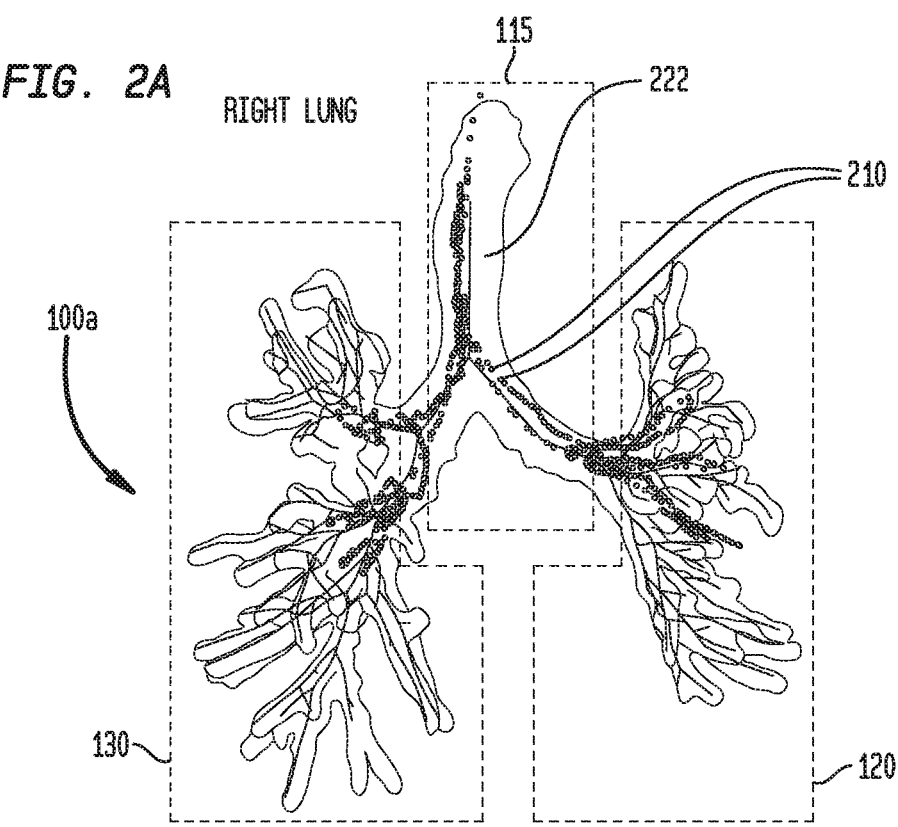
FIG. 2A-2D are illustrations of 3D volumetric models with survey points overlaid, provided in accordance with an embodiment of the present disclosure.
Figure 2B:
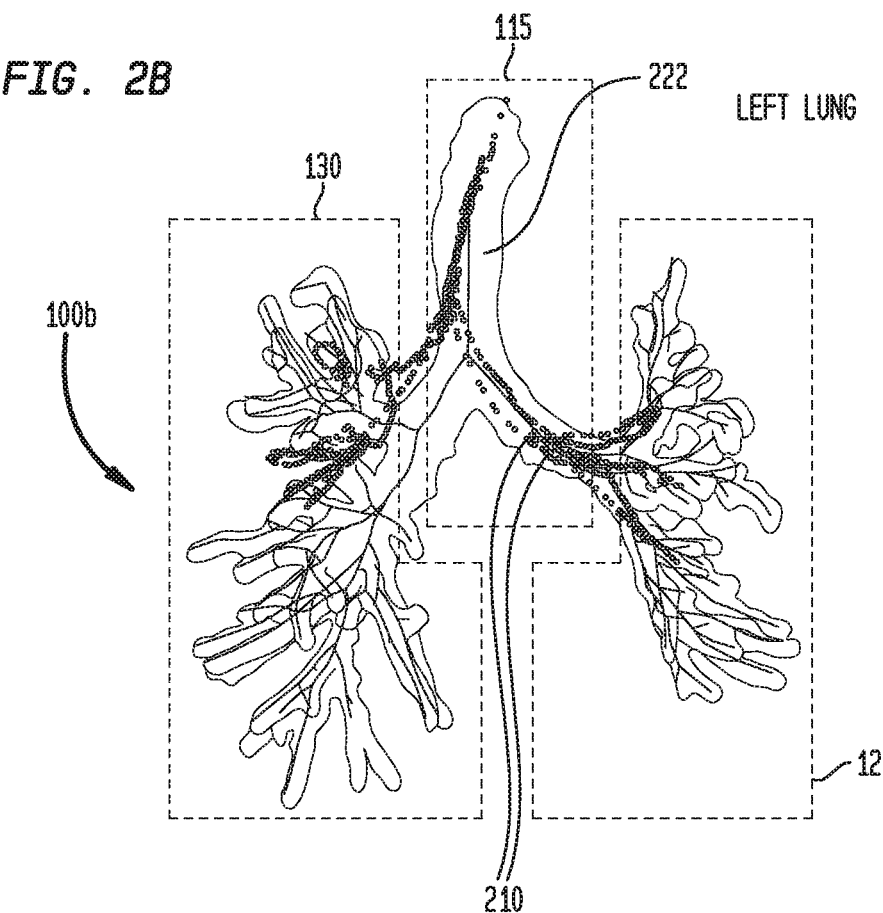
Figure 2C:
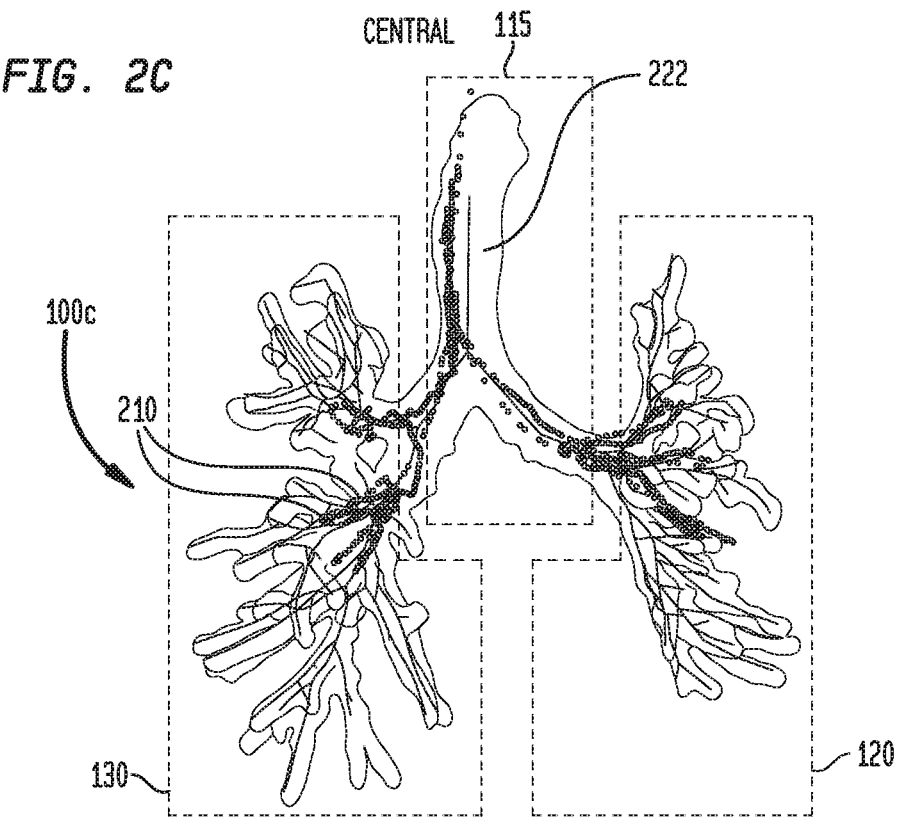
Figure 2D:
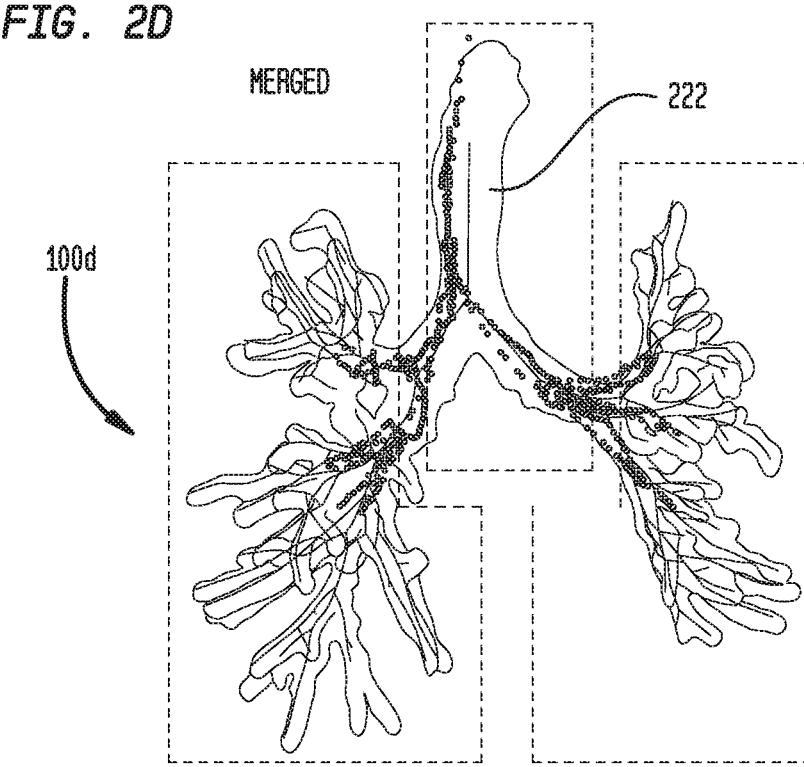

In multi-rigid registration, each of the plurality of regions is associated with a separate registration. For example, in one embodiment, central region 115, left lung region 120, and right lung region 130 each will have a separate registration (FIGS. 2A-2C). In further embodiments, each registration may be merged into a single registration (FIG. 2D).

Right-central region 135 is the volume of the airways where navigation is required to travel to transfer between right lung region 130 and central region 115. Left-central region 125 is the volume of the airways where navigation is required to travel to transfer between left lung region 125 and central region 115. As further described in the detailed description of FIGS. 3A and 3B, it is contemplated that within the right-central region 135 and the left-central region 125, the registrations for adjacent regions are used to interpolate a location of the EM sensor 94 and/or surgical tool 402 as it transitions between regions. The number of regions and the location and arrangement of regions are exemplary, and other numbers, locations, and arrangement of regions are contemplated to be within the scope of the present disclosure. For example, a particular arrangement of regions can include a region for a target lobe region, a region for the other lobe, and transition regions to the lobes. Other arrangements are contemplated.

Figure 4:
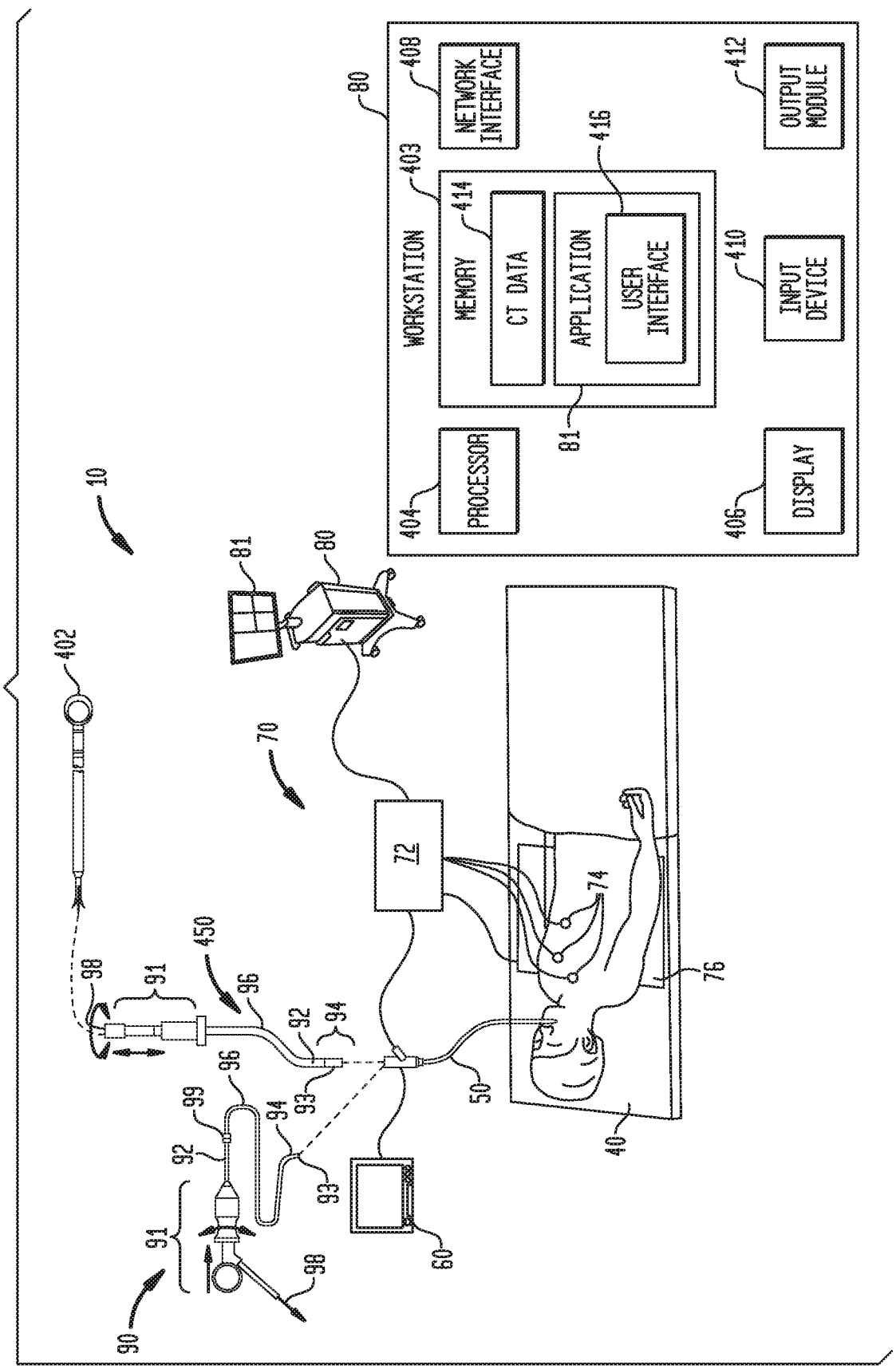
FIG. 4 is a perspective view of an electromagnetic navigation system and a schematic diagram of a workstation, provided in accordance with an embodiment of the present disclosure.

Furthermore, included within 3D model 100 are a plurality of reference points 110, which are selected within airway tree 102 and create reference airway tree 122. The plurality of reference points 110 are used as registration targets for the locations of EM sensor 94 (FIG. 4) and/or surgical tool 402 (FIG. 4), which are used to generate plurality of survey points 210 (shown in FIGS. 2A-2D) as EM sensor 94 and/or surgical tool 402 is advanced through the patient's airways. In various embodiments, the plurality of reference points 110 each includes x, y, and z coordinates which are recorded and stored in memory 403 (FIG. 4). Although Cartesian coordinates are used in the present disclosure for simplicity, it is contemplated that a different coordinate system can be used, such as spherical coordinates, cylindrical coordinates, or other coordinate systems. Such other coordinate systems are contemplated to be within the scope of the present disclosure.

Referring now to FIGS. 2A-2D, four views of different registrations 100a, 100b, 100c, and 100d, respectively, of the patient's airways are shown and each includes central region 115, left lung region 120, and right lung region 130 with plurality of survey points 210 obtained from the locations of EM sensor 94 and/or surgical tool 402 which create survey airway tree 222. With reference also to FIG. 4, during electromagnetic navigation, EM sensor 94 and/or surgical tool 402, in conjunction with tracking system 70, enables tracking of EM sensor 94 and/or surgical tool 402 as it is advanced through the patient's airways. EM sensor 94 may be incorporated into surgical tool 402 or different types of tools, such as a biopsy tool, microwave ablation tool, surgical stapling tools, radiotherapy ink application tools, etc., and enables determination of the current location of the tools. As EM sensor 94 and/or surgical tool 402 is advance through the patient's airways the x, y, and z coordinates of EM sensor 94 and/or surgical tool 402 are obtained at predetermined distance intervals and are stored in memory 403. In closer proximity to one or more targets 104 (FIG. 1), the predetermined distance intervals may be decreased, thus increasing the number of plurality of survey points 210 obtained. Following an electromagnetic navigation, all plurality of survey points 210 are obtained and may be overlaid onto 3D model 100. Plurality of survey points 210 are used in conjunction with plurality of reference points 110 in order for rigid registration to be performed.

During rigid registration, the goal is to find the alignment between the survey airway tree 222, created by the locations of plurality of survey points 210 and reference airway tree 122, created by plurality of reference points 110, which results in minimal "divergence" between local airways, as explained by the following. The rigid registration essentially corrects the global displacement between reference airway tree 122 and survey airway tree 222. In rigid registration, the minimum distance from each survey point 210 to a prospective transformation of reference airway tree 122 is determined. In the case of rigid registration, the "divergence" can be an average of the minimum distances. (Divergence in the case of multi-rigid registration will be described below herein.) In rigid registration, the divergence metrics for prospective transformations are compared, and the transformation corresponding to the minimum divergence is selected as the transformation to use for the rigid registration. That is, the transformation enables conversion of locations in the patient's airways to locations or coordinates in the 3D model based on CT scans. By applying the Automatic Registration technique, described in commonly owned U.S. Patent Publication No. 2011/0085720, and using plurality of reference points 110 and plurality of survey points, the reference airway tree 122 can become correlated with the survey airway tree 222 such that EM sensor coordinates can be translated to reference airway tree coordinates (also referred to herein as CT coordinates). For example, the rigid transformation may provide a slight rotation of reference airway tree 122, such that after the rotation reference airway tree 122 is more closely aligned with survey airway tree 222. Following rigid registration, the x, y, and/or z coordinates of plurality of reference points 110 will effectively be mapped to the plurality of survey points 210, without altering the 3D model from the CT scan. The particular manner of determining divergence disclosed above is exemplary. Generally, divergence as used herein refers to a metric that quantifies degrees to which a survey airway tree is aligned or not aligned with a reference airway tree. Other ways of determining divergence are contemplated to be within the scope of the present disclosure.

Multi-rigid registration is performed after the rigid registration. As used herein, multi-rigid registration refers to a collection of optimized region registrations. As explained below, optimized region registration seeks to align a particular region of a reference airway tree as closely as possible with the corresponding region of the survey airway tree, while taking into account to a lesser extent the overall alignment of other regions of the airway tree. Optimized region registration is performed for each region of the airway tree, and this entire process is referred to as multi-rigid registration.

In accordance with aspects of the present disclosure, during multi-rigid registration and optimized region registration, as further described herein, it is contemplated that each of the plurality of regions will have weight assigned, which is used to determine the amount that each region of reference airway tree 122 is able to be aligned with the corresponding region of survey airway tree 222. The weight assigned to each of the plurality of regions is also applied to plurality of survey points 210 located within that region, as explained below. Generally, during rigid registration, the alignment between reference airway tree 122 and survey airway tree 222 is such that the divergence described above is minimized. In contrast, during multi-rigid registration/ optimized region registration, different regions of the airway tree are weighted differently such that regions with larger weights are favored in the process of minimizing the divergence. For example, suppose a survey airway tree has two regions A and B, and the region weights are 0.9 for region A and 0.1 for region B. The weight of 0.9 is distributed evenly across all survey points of region A, and the weight of 0.1 is distributed evenly across all survey points of region B. For example, if region A has three (3) survey points, then each survey point in region A is assigned a weight of 0.9/3=0.3, and if region B has two (2) survey points, then each survey point in region B is assigned a weight of 0.1/2=0.05. In computing the divergence, the minimum distance from each survey point to a prospective transformation of the reference airway tree is multiplied by the weight assigned to the corresponding survey point, and the weighted minimum distances are averaged. Thus, in the case of multi-rigid registration/optimized region registration, the divergence is essentially a weighted average of the minimum distances, where survey points having greater weight will have a greater effect on the divergence. The divergence metrics for prospective transformations are compared, and the transformation corresponding to the minimum divergence is selected as the transformation to use. As explained above, this process for a particular region is referred to as optimized region registration. And as explained below in connection with FIGS. 2A-2C, the result of an optimized region registration is a particular registration that closely aligns the survey airway tree with the reference airway tree in the particular region. Thus, when there are multiple regions, optimized region registration is performed for each region, and the result is several separate registrations. The entire process of performing optimized region registration for all of the regions is what is referred to herein as multi-rigid registration. The particular way of determining divergence described above is exemplary, and other ways or determining divergence are contemplated to be within the scope of the present disclosure.

FIG. 2A illustrates a registration 100a of the patient's airway EM sensor readings with the 3D model of the airway after performing an optimized region registration with right lung region 130 more heavily weighted. Included within 3D model 100 are central region 115, left lung region 120, and right lung region 130. Additionally, 3D model 100 is shown together with the plurality of survey points 210. For FIG. 2A, right lung region 130 has been assigned a larger weight than both central region 115 and left lung region 120 and based on the larger weight assigned to right lung region 130, the airways of right lung region 130 of 3D model 100 are aligned more closely with survey points 210 within right lung region 130 than those survey points 210 within central lung region 115 and left lung region 120. Thus, while performing the optimized region registration while right lung region 130 is more heavily weighted, the alignment of plurality of reference points 110 and 3D model 100 with plurality of survey points 210 minimizes alignment differences within right lung region 130 while taking into account, to a lesser extent, the alignment differences of left lung region 120 and central lung region 115.

In contrast to FIG. 2A, in FIG. 2B, left lung region 120 is illustrated as being assigned a larger weight than both right lung region 130 and central region 115 and thus the patient's airways of left lung region 120 of 3D model 100 are aligned with survey points 210 within left lung region 120 more closely than those survey points 210 within central lung region 115 and right lung region 130. Similarly, in FIG. 2C, central region 115 is assigned a higher weight than that of left lung region 120 and right lung region 130, and the airways of central region 115 of 3D model 100 are aligned with survey points 210 within central region 115 more closely than those survey points 210 within left lung region 120 and right lung region 130.

It is contemplated that each registration, 100a, 100b, and 100c, may be used during navigation within right lung region 130, left lung region 120, and central region 115, respectively. Thus, as EM sensor 94 and/or surgical tool 402 is advanced through the patient's airways and the location of EM sensor 94 and/or surgical tool 402 is determined, a corresponding registration 100a, 100b, or 100c may be used.

Turning now to FIG. 2D, an illustration of a "merged" registration 100d is shown. FIG. 2D shows the registration of central region 115, as shown in FIG. 2C, the registration of left lung region 120, as shown in FIG. 2B, and the registration of right lung region 130, as shown in FIG. 2A. Thus, updated 3D model 100d provides a merged registration of the patient's airways using parts of the registrations of FIGS. 2A-2C and provides a more accurate registration of all regions of the airways.

Figure 3A:
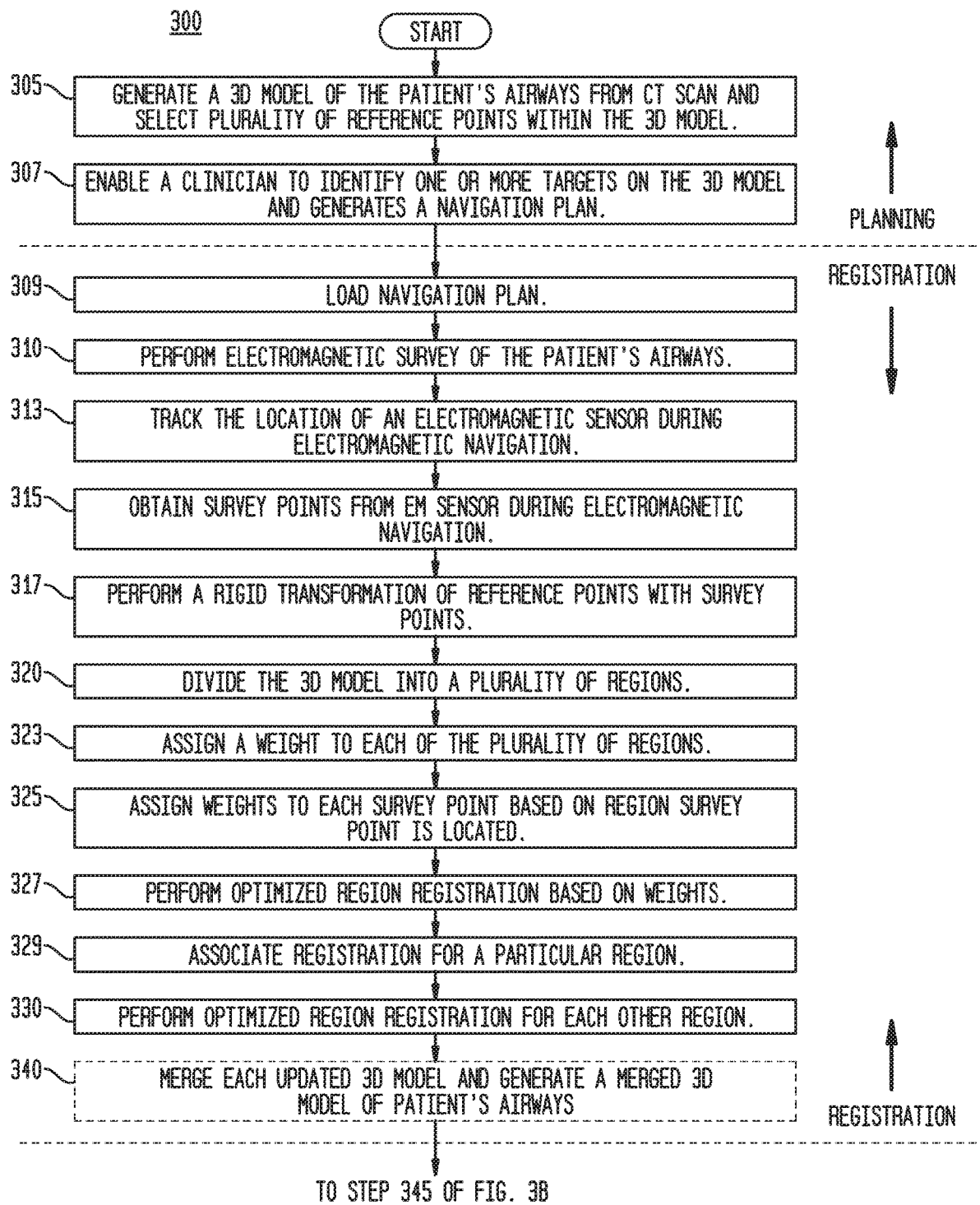

FIGS. 3A and 3B illustrate a flowchart of method 300. Flow chart 300 details registering multiple electromagnetic registrations of a luminal network to a 3D model of the luminal network using a weight metric based on the location of EM sensor 94 and/or surgical tool 402 and dynamically determining which of the multiple registrations is to be used, while navigation is in progress. Method 300 may be implemented, at least in part, by processor 404 executing instructions stored in the memory 403 (FIG. 4). Additionally, the particular sequence of steps shown in method 300 is provided by way of example and not limitation. Thus, the steps of method 300 may be executed in sequences other than the sequences shown in FIG. 3 without departing from the scope of the present disclosure. Further, some steps shown in the methods 300 may be concurrently executed with respect to one another instead of sequentially executed with respect to one another.

Referring now to FIG. 3A, method 300 begins at step 305, where 3D model 100 is generated based on the patient's CT scan or is accessed, and plurality of reference points 110 are selected within 3D model 100. At step 307, the clinician identifies one or more targets 104 on 3D model 100 and generates a navigation plan based on 3D model 100. At steps 309-340, the clinician begins the registration procedure. At step 309, the clinician loads the navigation plan generated at step 307. Next, at step 310, registration begins with the insertion of an EM sensor and bronchoscope into the patient to conduct a survey of the patient's airways. EM sensor 94, in conjunction with tracking system 70, enables tracking of EM sensor 94 and/or surgical tool 402 as EM sensor 94 and/or surgical tool 402 is advanced through the patient's airways, at step 313. Next, at step 315, processor 404, based on data from tracking system 70, obtains plurality of survey points 210 within the patient's airways during navigation.

Next, at step 317, after all plurality of survey points 210 are obtained, a rigid registration is performed between plurality of reference points 110 and reference airway tree 122, and plurality of survey points 210 and reference airway tree 222, as described above herein. Based on the rigid registration, a mapping or translation between the locations of plurality of reference points 110 and the plurality of survey points is generated. The rigid registration allows the survey points 210 to be correlated with the reference airway tree 122 so that each survey point 210 can be associated with a particular region of the reference airway tree 122 in preparation for multi-rigid registration. Next, at step 320, after updating 3D model 100, 3D model 100 is divided into a plurality or regions, for example, central region 115, left lung region 120, right lung region 130, right-central region 135, and left-central region 125, as shown in FIG. 1. Each region is assigned a weight, at step 323, as described in the detailed description of FIGS. 2A-2D and, at step 325, plurality of survey points 210 are assigned weights based on the weight assigned to the region where each survey point 210 is located. Next, at step 327, an optimized region registration is performed based on the weights assigned to each region, as described in the detailed description of FIGS. 2A-2D. At step 329, based on the optimized region registration, the registration is associated with a particular region. Next, at step 330, a separate registration, such as registrations 100a, 100b, and 100c, for each of the plurality of regions is generated based on performing optimized region registration with weights that favor a different region each time, as shown in FIGS. 2A-2C. It is contemplated that registrations 100a, 100b, and 100c may be stored in memory 403 (FIG. 4).

Optionally, at step 340, each registration, generated at steps 329 and 330, may be merged into a single registration, such as registration 100d. Thus, following the multi-rigid registration procedure of steps 310-340, multiple registrations are generated.

Referring now to FIG. 3B, method 300 continues from step 345 to step 378, where navigation and use of 3D model 100 during the surgical procedure is performed. At step 345, 3D model 100 is loaded and presented to a user. Additionally, the clinician then loads a navigation plan based on the 3D model loaded at step 345, the navigation plan including one or more targets 104. Thereafter, the clinician loads the navigation plan into application 81 from memory 403, a USB device, or from network interface 208. The navigation plan may require that all or only some regions of the patient's lungs be registered. Following the navigation plan, electromagnetic navigation is performed towards one or more targets 104, at step 350.

Turning now to step 355, EM sensor 94, in conjunction with tracking system 70, enables tracking of EM sensor 94 and/or surgical tool 402 as EM sensor 94 and/or surgical tool 402 is advanced through the patient's airways and processor 404 tracks the location of EM sensor 94 and/or surgical tool 402. At step 360, processor 404 and tracking system 70 in conjunction with EM sensor 94 and/or surgical tool 402 determines which region of the patient's airways EM sensor 94 and/or surgical tool 402 is located, based on the division of regions as described in step 320. In various embodiments, the processor 404 is configured to assume that the EM sensor 94 is in the same region that it was previously in. Next, at step 365, based on the region of the patient's airways EM sensor 94 and/or surgical tool 402 is located, the corresponding registration of the patient's airways (FIG. 2A-2C) is selected and used by the processor 404 to determine the location of the EM sensor 94 within the 3D model. For example, if the processor 404 determines that the EM sensor 94 is in the right lung region, then the registration 100a of FIG. 2A is selected and used, and the processor 404 determines the location of the EM sensor 94 within the 3D model 100 using that registration 100a. If the sensor location determined in step 365 is in a different region than the region selected in step 360, then step 365 is performed again to determine the location of the sensor using the registration for the new region.

Next, at step 367, processor 404 determines whether one or more targets 104 has been reached during navigation. If, at step 367, processor 404 determines that EM sensor 94 and/or surgical tool 402 has not reached target 104, method 300 continues to step 370 where processor 404 determines whether the location of EM sensor 94 and/or surgical tool 402 is transitioning between different regions of the patient's airways. For example, if processor 404 determines that the location of EM sensor 94 and/or surgical tool 402 is within right-central region 135 or left-central region 125, shown in FIG. 1.

If, at step 370, processor 404 determines that the location of EM sensor 94 and/or surgical tool 402 is not transitioning between different regions of the patient's airways (i.e., located in central region 115, left lung region 120, or right lung region 130), method 300 returns to step 355 and tracking of the location of EM sensor 94 and/or surgical tool 402 continues. If, at step 370, processor 404 determines that EM sensor 94 and/or surgical tool 402 is transitioning between regions (i.e., located in right-central region 135 and left-central region 125), method 300 proceeds to step 372 where, similar to that of step 355, tracking system 70, tracks the location of EM sensor 94 and/or surgical tool 402.

Next, at step 374, processor 404 determines in which transition region EM sensor 94 and/or surgical tool 402 is located and thus, which region EM sensor 94 and/or surgical tool 402 is transitioning out of and which region EM sensor 94 and/or surgical tool 402 is transitioning into. At step 376, processor 404 selects the registrations for the regions where EM sensor 94 and/or surgical tool 402 is transitioning out of and into and, at step 378, interpolates the location of the EM sensor using the two selected registrations. In various embodiments, the processor 404 interpolates the location of the EM sensor by computing the location $L_1$ of the EM sensor using the first registration and also computing the location $L_2$ of the EM sensor using the second registration. These two computed locations are used as the outer limits for the interpolation, such that the interpolated location of the EM sensor lies in between these two locations $L_1$ and $L_2$. In various embodiments, to determine the interpolated location, the processor 404 determines the distance $d_{11}$ from the first location to the first region, the distance $d_{12}$ from the first location to the second region, the distance $d_{21}$ from the second location to the first region, and the distance $d_{22}$ from the second location to the second region. In various embodiments, the average of $d_{11}$ and $d_{21}$ can be the average distance to the first region, and the average of $d_{12}$ and $d_{22}$ can be the average distance to the second region. If the average distance to the first region and the average distance to the second region are about the same, the interpolated location of the EM sensor can be about halfway between the two locations $L_1$ and $L_2$. Otherwise, the interpolated location of the EM sensor between $L_1$ and $L_2$ can be proportional to the average distance to the first region and the average distance to the second region. For example, if the average distance to the first region is 10 (arbitrary units) and the average distance to the second region is 20, the interpolated location can be $10/(10+20)=\frac{1}{3}$ of the way from $L_1$ to $L_2$, or equivalently, $\frac{2}{3}$ of the way from $L_2$ to $L_1$. The particular way of determining the interpolated location is exemplary, and other ways of interpolating location of the EM sensor are contemplated to be within the scope of the present disclosure.

After step 378, method 300 returns to step 367 where processor 404 determines whether EM sensor 94 and/or surgical tool 402 has reached target 104. If, at step 367, processor 404 determines that EM sensor 94 and/or surgical tool 402 has reached target 104, the currently generated 3D model is used and method 300 ends.

What has been described above is a method for registering bronchoscope sensor survey points with reference points in a 3D model, and using the registration during navigation of an airway luminal network. In accordance with aspects of the present disclosure, the disclosed method 300 can update the registration during navigation of the airway luminal network. In various embodiments, between steps 360 and 365 of FIG. 3B, the processor 404 can perform an optimized region registration using the location of the EM sensor determined in step 355. The weights for the optimized region registration can favor the region in which the EM sensor is located, which is determined at step 360.

Referring now to FIG. 4, electromagnetic navigation system 10 is provided in accordance with the present disclosure. One such electromagnetic navigation system is the ELECTROMAGNETIC NAVIGATION BRONCHOSCOPY® system currently sold by Medtronic PLC. Among other tasks that may be performed using electromagnetic navigation system 10 are planning a pathway to target tissue, navigating a positioning assembly to the target tissue, navigating a biopsy tool to the target tissue to obtain a tissue sample from the target tissue using the biopsy tool, digitally marking the location where the tissue sample was obtained, and placing one or more echogenic markers at or around the target.

Electromagnetic navigation system 10 generally includes an operating table 40 configured to support a patient; a bronchoscope 50 configured for insertion through the patient's mouth and/or nose into the patient's airways; monitoring equipment 60 coupled to bronchoscope 50 for displaying video images received from bronchoscope 50; a tracking system 70 including a tracking module 72, a plurality of reference sensors 74, and an electromagnetic (EM) field generator 76; a workstation 80 including software and/or hardware used to facilitate pathway planning, identification of target tissue, navigation to target tissue, and digitally marking the biopsy location FIG. 4 also depicts two types of catheter guide assemblies 90, 100. Both catheter guide assemblies 90, 100 are usable with electromagnetic navigation system 10 and share a number of common components. Each catheter guide assembly 90, 100 includes a handle 91, which is connected to an extended working channel (EWC) 96. EWC 96 is sized for placement into the working channel of a bronchoscope 50. In operation, a locatable guide (LG) 92, including an EM sensor 94, is inserted into EWC 96 and locked into position such that sensor 94 extends a desired distance beyond a distal tip 93 of EWC 96. The location of EM sensor 94, and thus the distal end of EWC 96, within an EM field generated by EM field generator 76 can be derived by tracking module 72, and workstation 80. Catheter guide assemblies 90, 100 have different operating mechanisms, but each contain a handle 91 that can be manipulated by rotation and compression to steer distal tip 93 of LG 92 and EWC 96. Catheter guide assemblies 90 are currently marketed and sold by Medtronic PLC under the name SUPERDIMENSION® Procedure Kits. Similarly, catheter guide assemblies 100 are currently sold by Medtronic PLC under the name EDGE™ Procedure Kits. Both kits include a handle 91, EWC 96, and LG 92.

As illustrated in FIG. 4, the patient is shown lying on operating table 40 with bronchoscope 50 inserted through the patient's mouth and into the patient's airways. Bronchoscope 50 includes a source of illumination and a video imaging system (not explicitly shown) and is coupled to monitoring equipment 60, e.g., a video display, for displaying the video images received from the video imaging system of bronchoscope 50.

Catheter guide assemblies 90, 400 including LG 92 and EWC 96 are configured for insertion through a working channel of bronchoscope 50 into the patient's airways (although the catheter guide assemblies 90, 400 may alternatively be used without bronchoscope 50). LG 92 and EWC 96 are selectively lockable relative to one another via a locking mechanism 99. A six degrees-of-freedom electromagnetic tracking system 70, e.g., similar to those disclosed in U.S. Pat. No. 6,188,355, and US Patent Publication No. 2014/0281961, the entire contents of each of which is incorporated herein by reference, or any other suitable positioning measuring system, is utilized for performing navigation, although other configurations are also contemplated. Tracking system 70 is configured for use with catheter guide assemblies 90, 400 to track the position of EM sensor 94 as it moves in conjunction with EWC 96 through the airways of the patient, as detailed below.

Electromagnetic field generator 76 is positioned beneath the patient. Electromagnetic field generator 76 and the plurality of reference sensors 74 are interconnected with tracking module 72, which derives the location of each reference sensor 74 in six degrees of freedom. One or more of reference sensors 74 are attached to the chest of the patient. The six degrees of freedom coordinates of reference sensors 74 are sent to workstation 80, which includes and application 81 which uses data collected by sensors 74 to calculate a patient coordinate frame of reference.

Also shown in FIG. 4 is a surgical instrument 402 that is insertable into catheter guide assemblies 90, 400 following navigation to a target and removal of LG 92. Surgical tool 402 may include and is not limited to, tissue collection tool, microwave ablation tool, surgical stapling tools, radiotherapy ink application tools, and the like. Surgical tool 402 is further configured for use in conjunction with tracking system 70 to facilitate navigation of surgical tool 402 to the target tissue, tracking of a location of surgical tool 402 as it is manipulated relative to one or more targets 404.

During procedure planning, workstation 80 utilizes computed tomographic (CT) image data for generating and viewing the 3D model of the patient's airways, enables the identification of target tissue on the 3D model (automatically, semi-automatically or manually), and allows for the selection of a pathway through the patient's airways to the target tissue. More specifically, the CT scans are processed and assembled into a 3D volume, which is then utilized to generate the 3D model of the patient's airways. The 3D model may be presented on a display monitor associated with workstation 80, or in any other suitable fashion. Using workstation 80, various slices of the 3D volume and views of the 3D model may be presented and/or may be manipulated by a clinician to facilitate identification of a target and selection of a suitable pathway through the patient's airways to access the target. The 3D model may also show marks of the locations where previous biopsies were performed, including the dates, times, and other identifying information regarding the tissue samples obtained. These marks may also be selected as the target to which a pathway can be planned. Once selected, the pathway is saved for use during the navigation procedure. Examples of a suitable pathway planning system and method are described in U.S. Patent Application Publication Nos. US 2014/0281961, US 2014/0270441, and US 2014/0282216, all entitled PATHWAY PLANNING SYSTEM AND METHOD, filed on Mar. 15, 2013, by Baker, the entire contents of each of which is incorporated herein by reference.

System diagram 400 of workstation 80 includes memory 403, processor 404, display 406, network interface 408, input device 410, and/or output module 412. Memory 403 includes any non-transitory computer-readable storage media for storing data and/or software that is executable by processor 404 and which controls the operation of workstation 80. In an embodiment, memory 403 may include one or more solid-state storage devices such as flash memory chips. Alternatively or in addition to the one or more solid-state storage devices, memory 403 may include one or more mass storage devices connected to the processor 404 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 404. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by workstation 80.

Memory 403 may store application 81 and/or CT data 414. Application 81 may, when executed by processor 404, cause display 406 to present user interface 616. Network interface 208 may be configured to connect to a network such as a local area network (LAN) consisting of a wired network and/or a wireless network, a wide area network (WAN), a wireless mobile network, a Bluetooth network, and/or the internet. Input device 510 may be any device by means of which a user may interact with workstation 50, such as, for example, a mouse, keyboard, foot pedal, touch screen, and/or voice interface. Output module 412 may include any connectivity port or bus, such as, for example, parallel ports, serial ports, universal serial busses (USB), or any other similar connectivity port known to those skilled in the art.

Memory 403 includes any non-transitory computer-readable storage media for storing data and/or software that is executable by processor 404 and which controls the operation of workstation 80. In an embodiment, memory 403 may include one or more solid-state storage devices such as flash memory chips. Alternatively or in addition to the one or more solid-state storage devices, memory 403 may include one or more mass storage devices connected to the processor 404 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 404. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by workstation 80.

What is claimed is:

1. A system for updating a 3D model of a luminal network, the system comprising:
   a computing device including a processor and a memory storing instructions which, when executed by the processor, cause the computing device to:
   access a 3D model of a luminal network inside a patient based on images of the luminal network;
   select a plurality of reference points within the 3D model of the luminal network;
   obtain a plurality of survey points within the luminal network;
   divide the 3D model of the luminal network into different regions of a lung;
   assign a plurality of weights to the different regions of the lung;
   determine an alignment of the plurality of reference points with the plurality of survey points based on the plurality of weights; and
   generate a registration based on the alignment.

2. The system according to claim 1, wherein the registration enables conversion of the plurality of survey points within the luminal network to points within the 3D model of the luminal network.

3. The system according to claim 1, wherein the instructions, when executed by the processor, further cause the computing device to:
   determine which region of the different regions of the lung in which each of the plurality of survey points is obtained; and
   assign a corresponding weight to each of the plurality of survey points based on the determined region in which each of the plurality of survey points is obtained.

4. The system according to claim 3, wherein the instructions, when executed by the processor, further cause the computing device to:

minimize a divergence between the plurality of reference points and the plurality of survey points based on the corresponding weight assigned to each of the plurality of survey points.

5. The system according to claim 1, wherein the instructions, when executed by the processor, further cause the computing device to:
for each particular region of the different regions of the lung:
assign a particular plurality of weights that favor the particular region;
minimize a divergence between the plurality of reference points and the plurality of survey points based on the particular plurality of weights, the minimized divergence corresponding to a particular alignment; and
generate a particular registration based on the particular alignment, the particular registration being associated with the particular region and enabling conversion of locations within the luminal network to locations within the 3D model of the luminal network.

6. The system according to claim 1, wherein the different regions of the lung include at least one transition region.

7. The system according to claim 6, wherein the different regions of the lung include a right lung region, a central region, and a left lung region, and the at least one transition region includes a left-central region and a right-central region.

8. A system for registering a patient's lung to a 3D model of the lung, the system comprising:
a computing device including a processor and a memory storing instructions which, when executed by the processor, cause the computing device to:
access a 3D model of a patient's lung based on images of the lung;
select a plurality of reference points within the 3D model;
obtain a plurality of survey points within the lung;
divide the 3D model into different regions of the lung;
assign a plurality of weights to the different regions of the lung;
determine an alignment of the plurality of reference points with the plurality of survey points based on the plurality of weights; and
generate a registration based on the alignment.

9. The system according to claim 8, wherein the instructions, when executed by the processor, further cause the computing device to:
determine which region of the different regions of the lung in which each of the plurality of survey points is obtained; and
assign a corresponding weight to each of the plurality of survey points based on the determined region in which each of the plurality of survey points is obtained.

10. The system according to claim 9, wherein the instructions, when executed by the processor, further cause the computing device to:
minimize a divergence between the plurality of reference points and the plurality of survey points based on the corresponding weight assigned to each of the plurality of survey points.

11. The system according to claim 8, wherein the instructions, when executed by the processor, further cause the computing device to:
for each particular region of the different regions of the lung:
assign a particular plurality of weights that favor the particular region;
minimize a divergence between the plurality of reference points and the plurality of survey points based on the particular plurality of weights, the minimized divergence corresponding to a particular alignment; and
generate a particular registration based on the particular alignment, the particular registration being associated with the particular region and enabling conversion of locations within the luminal network to locations within the 3D model of the luminal network.

12. A method of registering a luminal network to a 3D model of the luminal network, the method comprising:
selecting a plurality of reference points within a 3D model of a luminal network;
obtaining a plurality of survey points within the luminal network;
dividing the 3D model of the luminal network into different regions of a lung;
assigning a plurality of weights to the different regions of the lung;
determining an alignment of the plurality of reference points with the plurality of survey points based on the plurality of weights; and
generating a registration based on the alignment.

13. The method according to claim 12, wherein the luminal network is an airway of a patient.

14. The method according to claim 13, wherein the 3D model is a model of the airway of the patient.

15. The method according to claim 12, further comprising:
determining which region of the different regions of the lung in which each of the plurality of survey points is obtained; and
assigning a corresponding weight to each of the plurality of survey points based on the determined region in which each of the plurality of survey points is obtained.

16. The method according to claim 15, wherein determining an alignment of the plurality of reference points with the plurality of survey points includes minimizing a divergence between the plurality of reference points and the plurality of survey points based on the corresponding weight assigned to each of the plurality of survey points.

17. The method according to claim 12, further comprising:
for each particular region of the different regions of the lung:
assigning a particular plurality of weights that favor the particular region;
minimizing a divergence between the plurality of reference points and the plurality of survey points based on the particular plurality of weights, the minimized divergence corresponding to a particular alignment; and
generating a particular registration based on the particular alignment, the particular registration being associated with the particular region and enabling conversion of locations within the luminal network to locations within the 3D model of the luminal network.

18. The method according to claim 12, wherein the different regions of the lung include at least one transition region.

19. The method according to claim 18, wherein the different regions of the lung include a right lung region, a central region, and a left lung region, and the at least one transition region includes a left-central region and a right-central region.

20. The method according to claim 12, wherein the 3D model is based on computed tomography (CT) images of the luminal network.

* * * * *